United States Patent [19]

Treptow et al.

[11] Patent Number: 4,624,969
[45] Date of Patent: Nov. 25, 1986

[54] CROSSLINKED SILANE-FUNCTIONAL VINYLIDENE CHLORIDE POLYMER AND FILMS OR FOAMS THEREFROM

[75] Inventors: Warren L. Treptow, Midland, Mich.; Chung P. Park, Pickerington, Ohio; Kun S. Hyun, Midland, Mich.

[73] Assignee: The Dow Chemical Company, Midland, Mich.

[21] Appl. No.: 830,038

[22] Filed: Feb. 18, 1986

[51] Int. Cl.[4] .............................................. C08J 9/18
[52] U.S. Cl. ...................................... 521/60; 264/53; 521/56; 521/145; 521/154; 526/279
[58] Field of Search ................. 526/279; 521/60, 56, 521/145, 154

[56] References Cited

U.S. PATENT DOCUMENTS

| Re. 28,780 | 4/1976 | Bergmeister et al. | 525/158 |
|---|---|---|---|
| 2,848,427 | 8/1958 | Rubens | 521/97 |
| 3,983,080 | 9/1976 | Suh | 521/145 |
| 4,009,138 | 2/1977 | Kobashi et al. | 524/460 |
| 4,016,116 | 4/1977 | Poy | 521/74 |
| 4,042,556 | 8/1977 | Yoshinaga | 521/60 |
| 4,123,477 | 10/1978 | Watanabe et al. | 525/192 |
| 4,211,684 | 7/1980 | Koyama et al. | 526/273 |
| 4,291,090 | 9/1981 | Kenji et al. | 428/327 |
| 4,336,171 | 6/1982 | Kohlstadt et al. | 524/510 |
| 4,371,677 | 2/1983 | Morningstar et al. | 526/80 |
| 4,434,272 | 2/1984 | Keogh | 525/100 |
| 4,550,003 | 10/1985 | Sakata et al. | 521/60 |

OTHER PUBLICATIONS

Chemical Abstracts, vol. 90, 24295j, 1979.

*Primary Examiner*—Morton Foelak
*Attorney, Agent, or Firm*—Timothy W. Hagan

[57] ABSTRACT

A polymeric composition is provided which includes the reaction product of vinylidene chloride, an optional copolymerizable monomer, and an $\alpha,\beta$ ethylenically unsaturated silane crosslinking agent. The polymeric reaction product may also be used to form films and coatings. The composition further may include a volatile blowing agent which, when activated, expands the polymeric reaction product into a low density cellular structure.

3 Claims, 2 Drawing Figures

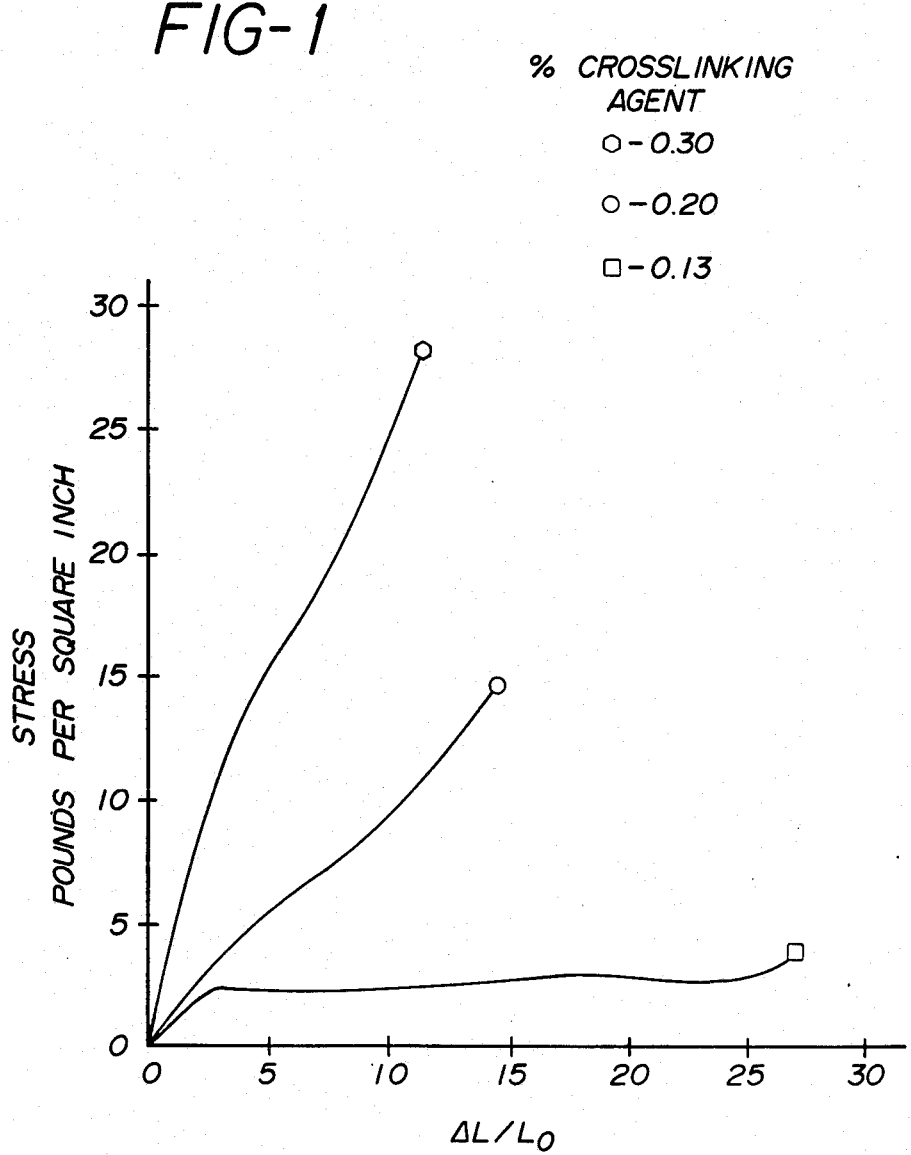

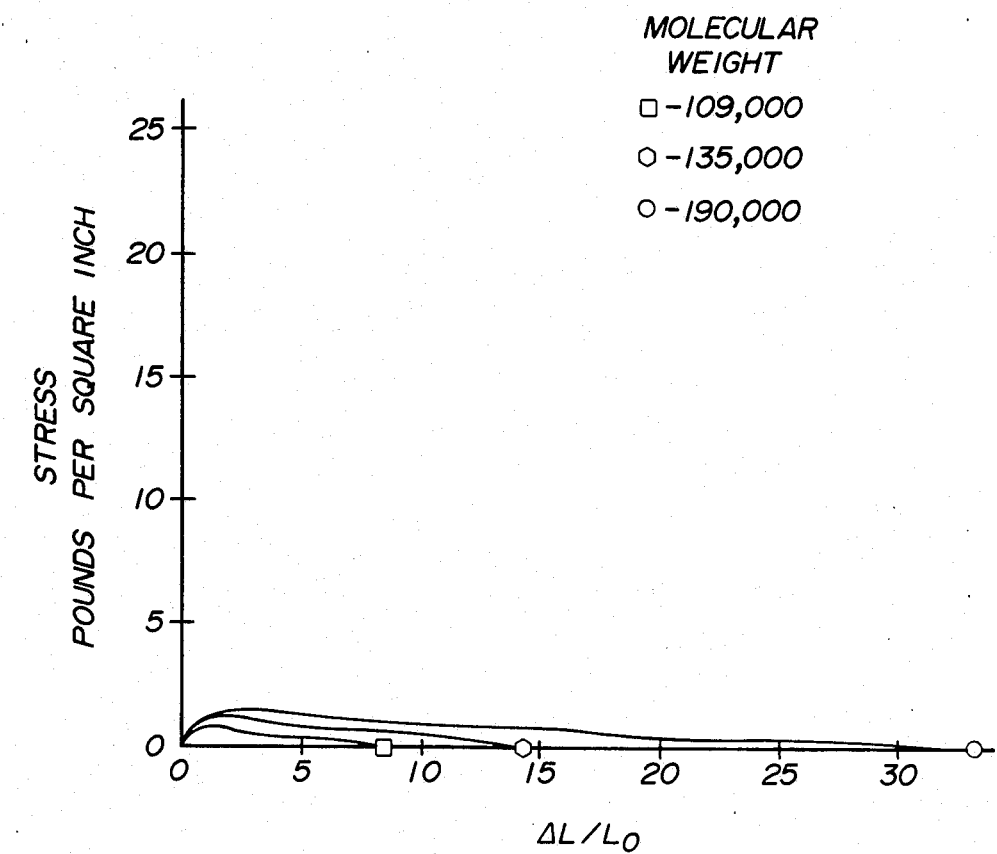

CROSSLINKED SILANE-FUNCTIONAL VINYLIDENE CHLORIDE POLYMER AND FILMS OR FOAMS THEREFROM

BACKGROUND OF THE INVENTION

This invention relates to a lightly crosslinked silane functional vinylidene chloride homopolymer or copolymer suitable for use as a film, coating, or foam, and more particularly to a polymer composition and process which is the reaction product of vinylidene chloride, an optional copolymerizable monomer, and an $\alpha,\beta$ ethylenically unsaturated silane.

Vinylidene chloride polymers are known to possess desirable chemical and physical properties including resistance to ignition and combustion, toughness, insolubility in common solvents, and low vapor and gas transmission rates. Such polymers have heretofore been used in synthetic fibers, coatings, and films. However, vinylidene chloride polymers, being essentially linear polymers, are known to have poor melt strengths. Moreover, polymers of vinylidene chloride have not been readily adaptable to conventional extrusion techniques used to produce foamed cellular structures. This has been due to several factors.

Initially, polymers of vinylidene chloride tend to degrade with the evolution of hydrogen chloride at temperatures only slightly above the temperatures necessary for melt processing. Additionally, most vinylidene chloride polymers, being essentially linear in nature, have poor melt tension. A sharp decrease in melt viscosity occurs at melt processing temperatures which results in poor foam quality and many open cells. Finally, vinylidene chloride polymers are insoluble or only somewhat soluble with many conventionally used blowing agents.

Attempts have been made to produce foams of polyvinylidene chloride. For example, Suh et al, U.S. Pat. No. 3,983,080, teach forming foams of normally crystalline vinylidene chloride and copolymerizable monomers utilizing blowing agents having specified physical properties and solubility characteristics and utilizing carefully controlled temperatures. Suh et al also discuss other prior art efforts at producing vinylidene chloride polymer foams.

Hattori et al, Japanese Kokai No. 78/112,967, have reported producing an extruded foam utilizing a mixture of polymers containing 60% polyethylene, 20% ethylene/vinyl acetate copolymer, and 20% polyvinylidene chloride copolymerized with polyolefins or polystyrene. However, it is believed that as the vinylidene chloride content of the foam is lowered, the effects of the desirable chemical and physical properties of vinylidene chloride are lessened.

Because of the poor melt strength of vinylidene chloride polymers, after heating and melting, some prior art techniques required that the polymer be cooled to increase melt strength prior to foaming. This required careful temperature control and very narrow workable temperature ranges. While the melt strength of such vinylidene chloride polymers may be increased by the introduction of crosslinking monomers such as diallyl ether, divinyl benzene, or diacrylates to produce higher molecular weight, crosslinked vinylidene chloride polymers, such higher molecular weight polymers would be unacceptable in an extrusion process. Such higher molecular weights would lead to the generation of shear heat in the extruder which would cause degradation of the vinylidene chloride polymer.

Accordingly, the need exists in the art for a vinylidene chloride polymeric composition and process for making it which possesses good melt strength and melt tension and which can be utilized in conventional melt processing techniques.

SUMMARY OF THE INVENTION

The present invention provides a polymeric composition which can be made into either a film, a coating, or a low density closed-cell foam utilizing conventional techniques such as extrusion and expansion of polymer beads. The composition comprises a unique reaction product of vinylidene chloride, an optional copolymerizable monomer, and an $\alpha,\beta$ ethylenically unsaturated silane crosslinking agent. Where a foam is desired, the composition further includes a volatile blowing agent which, when activated, expands the polymeric reaction product into a low density foam. Additional compatible stabilizers, plasticizers, and processing agents may also be included.

The polymeric reaction product has silane functionality. This functionality provides the reaction sites for a crosslinking reaction which occurs at an optimum time during melt processing and thereby minimizes the generation of shear heat and enables the polymer to be extruded and foamed with minimum degradation.

The resulting foam can be used as insulation because of its relatively low density, resistance to chemicals, ignition, and combustion, and has low thermal conductivity and vapor and gas transmission rates. Further, because of its toughness, flexibility, and resistance to breakage, the foam of the present invention can be used as cushioning in packaging or carpet padding. When used as a film or coating, the polymer of the present invention possesses the desirable physical and chemical properties of vinylidene chloride polymers and yet is more readily processable, having improved melt strength and melt tension.

Accordingly, it is an object of the present invention to provide a lightly crosslinked silane functional vinylidene chloride reaction product suitable for use as a film, coating, or, in the addition of volatile blowing agent, a foam. This, and other objects and advantages of the invention will become apparent from the following detailed description, the accompanying drawings, and the appended claims.

BRIEF DESCRIPTION OF THE DRAWINGS

FIGS. 1 and 2 are graphs of the stress-strain behavior of vinylidene chloride resins with no crosslinking (FIG. 1) and with silane functional crosslinking (FIG. 2).

DESCRIPTION OF THE PREFERRED EMBODIMENTS

The polymeric composition of the present invention is the result of the reaction between vinylidene chloride and an $\alpha,\beta$ ethylenically unsaturated silane. Optionally, a copolymerizable monomer may be included in the reaction. Such copolymerizable monomers include vinyl functional monomers such as vinyl chloride, alkyl esters of acrylic and methacrylic acids such as methyl acrylate, ethyl acrylate, methyl methacrylate, ethyl methacrylate, and ethylenically unsaturated mono- and dicarboxylic acids such as acrylic acid, methacrylic acid, and itaconic acid. Mixtures of such copolymerizable monomers may also be used.

The optional addition of such copolymerizable monomers reduces the degree of crystallinity in the reaction product and renders it more easily processable. However, relatively greater amounts of copolymerizable monomer in the reaction product will lower the serviceability of the foam at higher temperatures. Accordingly, it is preferred that if a copolymerizable monomer is utilized, that it be added to the reactants in an amount of from between 1–99% by weight. As the amount of silane added is typically quite small, i.e., 0.01 to 5.0%, the vinylidene chloride component of the reactants may be from 1 to 99.9% by weight, preferably from 50 to 99.9% by weight.

Additionally, conventional amounts and types of plasticizers, stabilizers, nucleators, and processing aids may be added to the reaction product. For example, the addition of from 1–2% by weight of a copolymer of ethylene and vinyl acetate, a copolymer of ethylene and methyl acrylate, or other polyolefins may facilitate mixing and impregnation of the volatile blowing agent or otherwise aid in the melt processability of the reaction product.

As the $\alpha,\beta$ ethylenically unsaturated silane reactant, any of a number of vinyl functional silane compounds may be utilized. For example, $\gamma$-methacryloxypropyltrimethoxy silane, $\gamma$-methacryloxypropyltriethoxy silane, vinyl trimethoxysilane, vinyl triethoxysilane, vinyl tris($\beta$-methoxy ethoxy)silane, and mixtures thereof may be reacted with vinylidene chloride to provide a silane functional polymeric reaction product. Such a reaction may be carried out utilizing conventional polymerization techniques including suspension polymerization.

Preferably, the polymeric reaction product has a weight average molecular weight of between 150,000 and 250,000, and preferably between 180,000 and 220,000. This average molecular weight permits ready melt processing of the polymer including melting, plasticizing, and mixing of the polymer with the volatile blowing agent. Higher molecular weight vinylidene chloride polymers would be subject to shear and polymer degradation during the initial phases of processing. This molecular weight would, however, normally be much too low to permit the production of a good quality low density foam. The melt strength of such a low molecular weight vinylidene chloride polymer would be inadequate for conventional extrusion foaming techniques.

However, the unique silane-functional reaction product of the present invention undergoes a light crosslinking reaction at an optimum point in the melt processing procedure to improve its melt strength through a chain extending crosslinking reaction which occurs at the silane functional sites. It has been found that only a small amount of silane crosslinking agent is needed, with the range being from about 0.005 to 5.0%, preferably 0.05 to 3.0%, on a mole basis. The optimum amount for improving processability of the melt is near the lower end of the above range. However, adding larger amounts of the silane to provide more reaction sites on the reaction product with vinylidene chloride will produce a more highly crosslinked structure and result in a cellular foam structure having a higher heat distortion temperature.

In the presence of trace amounts of water and acid, the polymer melt undergoes the following crosslinking reaction:

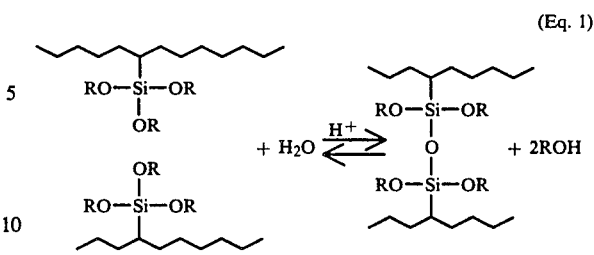

(Eq. 1)

where R is an alkyl group such as methyl or a $\beta$-methoxy ethyl group.

The crosslinking reaction is essentially self-catalyzing because sufficient trace moisture will almost always be present in the polymer. Likewise, at the processing temperatures utilized by the invention, there will be some slight degradation of the vinylidene chloride polymer with accompanying evolution of trace amounts of hydrochloric acid.

The crosslinking reaction may be further controlled to delay it until an optimum point in the process by drying the polymer before melt processing. Trace amounts of water may then be injected into the process at the appropriate time to initiate the crosslinking reaction. Alternatively, alcohol may be utilized as a secondary blowing agent and delay the above-noted reaction until the melt is taken to a zone of lower pressure, at which point the alcohol will vaporize and permit the crosslinking reaction shown in Eq. 1 to go to completion. The use of an alcohol in this manner is more fully explained in commonly assigned copending application Ser. No. 672,010, filed Nov. 16, 1984, entitled "Alcohol Control of Lightly Crosslinked Foamed Polymer Production."

The blowing agents utilized in the practice of the present invention may be any conventional compatible physical blowing agent. Preferred blowing agents include the group of halogenated hydrocarbon compounds having from 1 to 4 carbon atoms. The compounds include trichlorofluoromethane (FC-11), dichlorodifluoromethane (FC-12), dichlorotetrafluoroethane (FC-114), 1,1,2-trichlorotrifluoroethane (FC-113), methylene chloride, ethyl chloride, and mixtures thereof. As mentioned above, an alcohol such as methanol or ethanol may be utilized as a secondary blowing agent. When these halogenated hydrocarbon blowing agents are utilized, there can be from about 0.013 to about 0.50 gram mole of such blowing agent per 100 grams of polymeric reaction product in the polymer melt.

In accordance with a preferred embodiment of the invention, the silane functional reaction product may be made into foam on conventional melt processing apparatus such as by continuous extrusion from a screw-type extruder. Such an extruder typically comprises a series of sequential zones including a feed zone, melt zone, mixing zone, and cooling zone. The barrel of the extruder may be provided with conventional electric heaters for zoned temperature control. Typically, the volatile blowing agent will be injected into the mixing zone after the polymer had passed through the melt zone.

However, because of the tendency of vinylidene chloride polymers to degrade when heated to the necessary temperatures to melt process them, it is preferred that the blowing agent be incorporated into the polymer prior to melt processing. This may be accomplished by suspending the silane functional reaction product, in the form of small pellets or powder, in a suspending agent such as water and injecting blowing agent into the suspension while heating and agitating the suspension. In this manner, the preimpregnated polymer need not undergo substantial mixing in the extruder, and lower extruder temperatures may be utilized.

After sufficient mixing in the extruder, the hot polymer gel is passed through a temperature-controlled cooling zone, through a die orifice, and into a zone of lower pressure (i.e., ambient air atmosphere) where the blowing agent is activated and the polymer gel expands to a lower density cellular mass. As the foamed extrusion forms, it is conducted away from the die and allowed to cool and harden. The density of the foam ranges from about 9.6 to 400 Kg/m$^3$ (0.6 pcf to 25.0 pcf).

In practice, the temperature of the feed zone in the extruder is maintained at 150°±5° C., the temperature of the melting and mixing zones is maintained at 160°±5° C., and the temperature in the cooling and temperature control zone is maintained at 145°±6° C. The temperature of the polymer gel as it expands through the die orifice is preferably just above the temperature at which solid polymer would crystallize out of the gel and will vary depending upon the specific polymeric reaction product utilized.

Alternatively, the pelletized reaction product of the present invention may be impregnated with blowing agent, as discussed above, and may be expanded in pellet or bead form. The expanded beads may then be used to form molded foam products. Preferably, the expansion is carried out in steam or hot air at from 150°-160° C.

In yet another embodiment of the invention, the polymeric reaction product of the present invention may be formed into a film or coating. Such films or coatings will possess similar high gas barrier properties as prior art vinylidene chloride polymers. The lightly crosslinked reaction product of the present invention, with its enhanced melt strength and melt tension, would make it more readily processable in the manufacture of films utilizing conventional blown film technology.

In order that the invention may be more readily understood, reference is made to the following examples, which are intended to illustrate the invention but is not to be taken as limiting the scope thereof. All parts and percentages are by weight unless otherwise specified or required by the context.

EXAMPLE 1

The following monomeric coreactants were polymerized utilizing conventional suspension polymerization techniques:
6% methyl acrylate
93.87% vinylidene chloride
0.13% γ-methacryloxypropyl trimethoxysilane (available from Dow Corning under the designation Z-6030)
A polymeric reaction product having a weight average molecular weight of 190,000 was produced.

To 100 parts of reaction product, 1 part of tetrasodium pyrophosphate stabilizer and 2 parts dibutyl sebacate plasticizer were added. The reaction product was heated, and in the presence of trace amounts of water and acid, the silane functional polymeric reaction product underwent a crosslinking reaction in accordance with Eq. I, above.

The stress-strain behavior of conventional vinylidene chloride (Saran) molded resin was compared to that of a lightly crosslinked silane functional molded resin of the present invention. The extensional viscosity of molded resin samples was determined at 190° C. by applying a stress force on the sample.

FIG. 1 illustrates the extensional viscosities for three molded Saran resins at 190° C. The resins were copolymerized utilizing conventional suspension polymerization techniques using 6% methyl acrylate and 94% vinylidene chloride monomers. The resins had molecular weights of 109,000, 135,000, and 190,000, respectively.

As shown in FIG. 1, the application of a very low stress force of 1 psi or less resulted in large extension ratios ($\Delta L/L_o$, where $L_o$ is the original sample length and $\Delta L$ is the change in sample length) for all three samples. These results are indicative of resins possessing no melt strength.

FIG. 2 illustrates the extensional viscosities of three lightly crosslinked molded Saran resins prepared in accordance with the present invention at 190° C. The resins were copolymerized utilizing conventional suspension polymerization techniques using 6% methyl acrylate, from 93.7 to 93.87% vinylidene chloride, and from 0.13 to 0.3% γ-methacryloxypropyl trimethoxysilane as a crosslinking agent. The three resins all had molecular weights of approximately 190,000.

As shown in FIG. 2, these silane-functional resins displayed dramatic increases in the amount of stress applied to achieve large extensional ratios. These results are indicative of resins having significantly higher melt strengths than the uncrosslinked resins of FIG. 1.

EXAMPLE 2

An extruded polymeric foam was prepared as follows. A blend of 90 parts by weight of a silane-functional vinylidene chloride polymer and 10 parts by weight of a copolymer of methyl acrylate and vinylidene chloride was melt processed in an extruder at 180° C. for 1 minute. Pellets of the blend were produced. The silane-functional vinylidene chloride polymer was the reaction product of 6% methyl acrylate, 93.87% vinylidene chloride, and 0.13% γ-methacryloxypropyl trimethoxysilane (Dow Corning Z-6030). The copolymer component was the reaction product of 6% methyl acrylate and 94% vinylidene chloride. Both polymers had base molecular weights of 190,000. The blend also contained about 2 parts/hundred by weight of Elvax 3180 (trademark), a copolymer of 72% ethylene and 28% vinyl acetate (25 melt index), 1 part/hundred of tetrasodium pyrophosphate stabilizer, and 2 parts/hundred dibutyl sebacate plasticizer.

The pellets were impregnated to a level of about 12% trichlorofluoromethane (FC-11) blowing agent by exposure to the blowing agent at 85° C. for a period of 24 hours. The impregnated pellets were then melt processed in an extruder at 135° C. Additional FC-11 blowing agent was injected into the extruder.

The polymer gel was then expanded through a die orifice in the extruder to produce a cellular foam structure having a density of about 144 to 160 Kg/m$^2$ (9 to 10 pcf). The average cell size was less than 1 millimeter.

While the methods and compositions herein described constitute preferred embodiments of the invention, it is to be understood that the invention is not limited to these precise methods and compositions, and that changes may be made in either without departing from the scope of the invention, which is defined in the appended claims.

What is claimed is:

1. A process for the preparation of polymeric foam beads suitable for producing molded foam articles comprising the steps of:
   (a) reacting vinylidene chloride with a $\alpha,\beta$ ethylenically unsaturated silane to form a silane functional polymer in pellet or bead form,
   (b) impregnating a volatile blowing agent into said silane functional polymer, and
   (c) exposing said silane functional polymer to sufficient heat to activate said blowing agent and expand said silane functional polymer to a cellular cross-linked structure.

2. The process of claim 1 in which the reaction in step (a) further includes from 1–99% of a copolymerizable monomer selected from the group consisting of vinyl functional monomers, alkyl esters of acrylic and methacrylic acid, ethylenically unsaturated mono- and dicarboxylic acids, and mixtures thereof.

3. The process of claim 1 in which said silane is present in an amount of from 0.005 to 5.0% on a mole basis.

* * * * *